United States Patent [19]

Furuya

[11] Patent Number: 5,447,532
[45] Date of Patent: Sep. 5, 1995

[54] HIGHLY ABSORPTIVE EXPANDING THERAPEUTIC WATER PILLOW

[76] Inventor: Mitsuko Furuya, 8-18, Haruecho 2-chome, Edogawa-Ku, Tokyo, 132, Japan

[21] Appl. No.: 118,615

[22] Filed: Sep. 10, 1993

[51] Int. Cl.[6] .................................. A61F 7/00
[52] U.S. Cl. ............................. 607/114; 5/644
[58] Field of Search ............. 607/96, 108–112, 607/114; 5/451, 644

[56] References Cited

U.S. PATENT DOCUMENTS

| | | | |
|---|---|---|---|
| 2,710,008 | 6/1955 | Jensen | 607/114 |
| 4,106,478 | 8/1978 | Higashijima | 607/114 X |
| 4,325,254 | 4/1982 | Svacina et al. | 607/114 |
| 4,892,532 | 1/1990 | Boman | 604/366 |

FOREIGN PATENT DOCUMENTS 61-163622 10/1986 Japan.
63-109122 7/1988 Japan.
2-13523 1/1990 Japan.

*Primary Examiner*—Angela D. Sykes
*Attorney, Agent, or Firm*—Jacobson, Price, Holman & Stern

[57] ABSTRACT

A water pillow comprised of a closed bag made of cloth or nonwoven fabric having high water permeability. A water absorptive high polymer material is contained in the bag and expands with water absorption such that the expansion capacity defines the volume of the water pillow. A deodorant agent can be absorbed in the absorptive material in order to eliminate odors associated with sweat.

3 Claims, 1 Drawing Sheet

HIGHLY ABSORPTIVE EXPANDING THERAPEUTIC WATER PILLOW

BACKGROUND OF THE INVENTION

The present invention relates to an expanding water pillow which is quickly deployable for use.

A conventional water pillow (also known as an "ice bag"), is shown in FIG. 4 which holds water and ice inside a bag 1. The bag is made of rubber or vinyl and closed with a stopper 2. The temperature of the water pillow is affected by the mixture rate of water and ice contained therein, making it difficult to adjust the overall temperature of the ice bag.

Furthermore, in prior art water pillows, the moisture in the air condenses, making the surface of the pillow wet. Therefore, the pillow must be covered with a towel or the like, when in use. The same phenomenon occurs with water pillows covered by impermeable material such as Ice-non®. Moreover, the towel wrapped around the water pillow absorbs not only dew but also the sweat of the patient, generating an unpleasant odor.

It is desirable to provide a water pillow which has a controlled temperature, and which does not "sweat" like prior art ice bags.

SUMMARY OF THE INVENTION

The present invention is directed to a water pillow comprised of a closed bag made of cloth or nonwoven fabric having high water permeability. A water absorptive high polymer material is disposed in the bag. The amount of high polymer material controls the expansion capacity of the bag when the high polymer material absorbs water.

When in use, the water pillow is soaked in a container with (iced) water adjusted to a preferable temperature. The water penetrates through the water permeable bag and is absorbed by the absorptive material therein; thereby solidifying the high polymer material, expanding and defining the shape of the water pillow.

Moreover, the dew generated on the surface of the water pillow when in use is absorbed by the high polymer material inside. Therefore, the surface of the water pillow is kept substantially dry. Further, a deodorant agent may be disposed in the water absorptive high polymer material to eliminate unpleasant odors associated with sweat and the like.

DETAILED DESCRIPTION OF THE DRAWINGS

Figure 1:
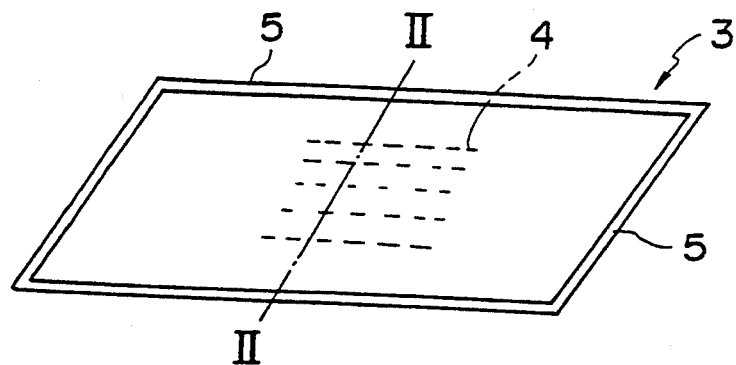
FIG. 1 is a schematic view showing the structure of the water pillow unfilled.
Figure 2:
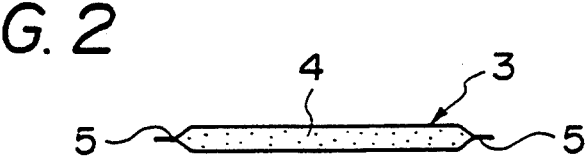
FIG. 2 is a cross-sectional view taken at line II—II of FIG. 1.

In FIGS. 1 and 2, the water pillow is shown generally at 3, formed in the shape of a bag. The walls of the bags are made of a water permeable material. A water absorptive high polymer material 4 is contained inside the bag. A peripheral portion 5 along the bag is sealed to contain the water absorptive high polymer material 4. Water passes through to the interior of the bag and is absorbed by the polymer material 4, and is thereby contained within the bag.

The amount of water absorptive high polymer material 4 stored inside the bag shaped water pillow 3 is chosen so that the pillow will expand to appropriate dimensions when water is absorbed. Further, the dew condensation formed on the outer surface of the water pillow and also the sweat of the patient is absorbed inside the water pillow, so that the outer surface of the water pillow is substantially dry.

The method of using the water pillow according to the present invention is as follows.

Figure 3:
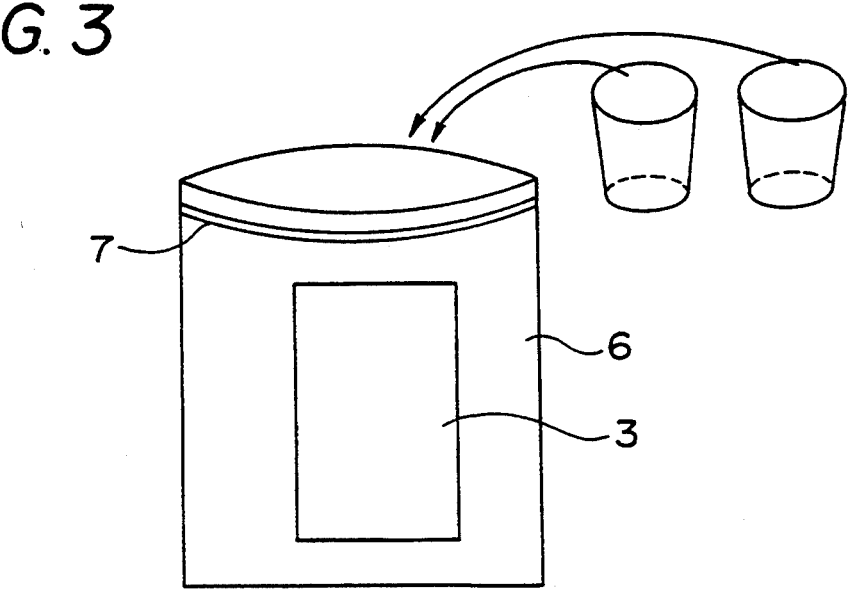
FIG. 3 is a schematic diagram showing the steps whereby the iced water is absorbed in the water pillow.
Figure 4:
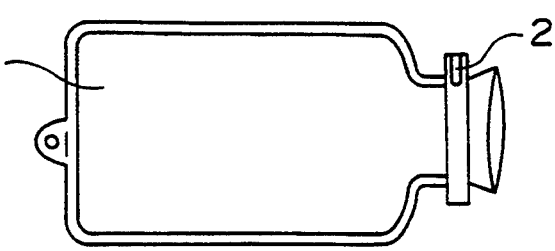
FIG. 4 is a side view of a prior art water pillow.

As shown in FIG. 3, a plastic bag 6 which is big enough to contain the water pillow 3 therein is prepared. The water pillow 3 is placed in the plastic bag 6 together with ice water adjusted to a preferable temperature. The ice water is absorbed into the water absorptive high polymer material 4 through the water permeable walls of the bag 3. Thus, the pillow will expand as the polymer material 4 absorbs the ice water. A fastener 7 is mounted on the plastic bag 6 to enclose the water pillow 3 and the ice water inside during this process. As the water pillow 3 expands, it has been found beneficial to gently hit the bag so as to quicken the absorption of the water into the bag 3 remaining inside the bag 6.

The expanded water pillow 3 (now the shape of a pillow) may be removed from the plastic bag 6 after the absorption of ice water by the high polymer material 4. The water pillow 3 can be used instantaneously.

Further, by keeping it in the refrigerator after use, the same water pillow could be re-used 3–5 times.

As one specific example, the water pillow may be constructed of (235×111 mm) nonwoven fabric and approximately 8 grams of high polymer absorptive material. The bag may weigh approximately 2.5 grams. A preferred water absorptive high polymer material is "Sunwet IM-5700-D" manufactured by Sanyo Chemical K.K. The high polymer material could absorb water up to about 100 times its volume, but it is recommended to use a volume of water not more than 50 times the volume of the polymer material. By feeding the water pillow 3 with 400 cc (2 cups) of ice water cooled to the desired temperature with ice as described in conjunction with FIG. 3, an effective water pillow shape can be realized.

The amount of water used should be chosen carefully, because with too much water, the bag could overswell, and possibly break. Also, if the amount of high polymer material is too small, the ability of the bag to absorb dew and sweat might not be sufficient.

The water pillow of the present invention may absorb the sweat and smell of a patient. To avoid infection, one pillow should only be used by the same person. Further, a used water pillow could be disposed.

The water pillow of the present invention has a flat shape when not in use, making it convenient to store and carry. Further, the temperature of the water absorbed by the water absorptive high polymer material may be adjusted beforehand, avoiding the possibility of overcooling. Moreover, the surface of the water pillow is kept dry because the dew does not stay and sweat on the surface. Rather, substantially all the moisture is absorbed by the high polymer material, keeping the sweat and its accompanying odor away from the user. Thus, it eliminates the need for a towel for preventing overcooling or for absorbing dew.

It also is possible to construct the water pillow with various shapes corresponding to the particular intended use.

Further, a deodorant agent may be absorbed in the absorptive material to deodorize the odor of sweat of the user which is absorbed by the water absorptive high polymer material. For example, "S.I.T." (granule state), manufactured by Leicy K.K., is an effective deodorant.

Although the water pillow has been described for cooling purposes state, it is to be understood that the pillow can also be used as a warming pillow by absorbing hot water.

The above description is intended by way of example only and is not intended to limit the present invention in any way, except as set forth in the following claims.

I claim:

1. A method for preparing a therapeutic water pillow for use comprising the steps of:

providing a therapeutic water pillow comprising a sealable bag made of water permeable material, and water absorptive material being disposed in said bag adapted to expand when absorbing water and thereby give volume to the water pillow;

placing said therapeutic water pillow in a larger sealable preparation bag;

placing an amount of water adjusted to a preferable temperature in the preparation bag, said amount being selected for providing a required amount of expansion to the water absorptive material which is less than the expansion capacity of the absorptive material whereby the absorptive material can absorb additional liquid when the water pillow is subsequently removed from the preparation bag for use;

sealing the preparation bag with the therapeutic water pillow and water therein to allow the water to pass through the sealable bag and be absorbed by the water absorptive material of the water pillow to thereby expand and deploy the water pillow for use; and removing the therapeutic water pillow from the preparation bag for use.

2. A method as claimed in claim 1 wherein the absorptive material is a high polymer material.

3. A method claimed in claim 1 further including absorbing a deodorant in the absorptive material.

* * * * *